United States Patent [19]
Lazarus et al.

[11] Patent Number: 5,415,633
[45] Date of Patent: May 16, 1995

[54] REMOTELY STEERED CATHETERIZATION DEVICE

[75] Inventors: Kenneth B. Lazarus, Boston; Edward E. Crawley, Cambridge, both of Mass.; Richard D. Fish, Houston, Tex.

[73] Assignee: Active Control Experts, Inc., Cambridge, Mass.

[21] Appl. No.: 98,205

[22] Filed: Jul. 28, 1993

[51] Int. Cl.$^6$ ............................................. A61M 37/00
[52] U.S. Cl. ...................................... 604/95; 604/281; 128/657; 128/772
[58] Field of Search .................. 604/95, 281; 128/657, 128/772

[56] References Cited

U.S. PATENT DOCUMENTS

| | | | |
|---|---|---|---|
| 4,799,474 | 1/1989 | Ueda | 604/281 |
| 4,838,859 | 6/1989 | Strassman | 604/95 |
| 4,921,482 | 5/1990 | Hammerslag et al. | |
| 4,934,340 | 6/1990 | Ebling et al. | 604/95 |
| 4,944,727 | 7/1990 | McCoy | 604/95 |
| 4,984,581 | 1/1991 | Stice | 604/95 |
| 5,238,005 | 8/1993 | Imran | 604/95 |
| 5,281,213 | 1/1994 | Milder et al. | 604/95 |

OTHER PUBLICATIONS

Pilot Cardiovascular Systems Inc. flyer.

*Primary Examiner*—C. Fred Rosenbaum
*Assistant Examiner*—Bryan Leander Tsosie
*Attorney, Agent, or Firm*—Lahive & Cockfield

[57] ABSTRACT

A remotely steerable guidewire, catheter or insertable active implement is disclosed. A steerable guidewire or a catheter for coronary and peripheral catheterizations is illustrated, using smart materials such as piezoelectrics for controlling its motions inside the body via control inputs applied from outside the body. A steerable portion of the device, which may be either an active flexible tip or an active region along the length of the implement, controls the shaft position or modifies its stiffness. In one embodiment, manipulation of electrical control inputs permits deflection of the steerable region through a range of motion about the axis of the implement in a single plane. In further embodiments, the tip may deflect in multiple planes about its longitudinal axis, or the catheter may be selectively stiffened to assume an arc shape or to firmly lodge the tip in position in a vessel.

26 Claims, 4 Drawing Sheets

REMOTELY STEERED CATHETERIZATION DEVICE

BACKGROUND OF THE INVENTION

The present invention relates to steering devices such as may be used with catheters, cannulae, guidewires and the like. More particularly, the present invention relates to catheters and guidewires that are steerable through body lumena or cavities, and are positioned within or aimed at obstructions, organs, or tissue within the body from a position external to the body.

Medical catheters generally comprise elongate tube-like members which may be inserted into the body, either percutaneously or via a body orifice, for any of a wide variety of diagnostic and interventional purposes. Such medical applications frequently require use of a catheter having the ability to negotiate twists and turns; this is particularly the case with regard to certain cardiovascular applications.

For such applications, the object is to reach and deliver some treatment or instrument to a remote lesion. Often, it is required that the instrument cross the lesion, which may consist of hard and inflexible tissue with a very rough surface, or even protruding flaps.

One such application, Percutaneous Transluminal Coronary Angioplasty (balloon angioplasty), requires manipulation of a catheter from a position outside the patient's body through extended portions of the patient's arterial system to the stenotic site for the purposes of alleviating the lesion by inflating a balloon. This particular procedure, performed with increasing frequency over the past years, is done in preference to open heart bypass surgery, when possible.

In a typical angioplasty procedure, a guidewire is transluminally inserted into the brachial or the femoral artery, to be positioned within the stenotic region and followed by a balloon catheter. The cardiologist usually pre-bends the distal tip of the guidewire before insertion and then rotates (or torques) the wire once it has reached a branch artery to enable the tip of the guidewire to enter the branch. If the angle of the bend needs to be adjusted, the guidewire is removed, re-bent and reinserted, sometimes several times during one angioplasty procedure. Particular difficulty is encountered with pre-bending in cases when an artery branches at one angle, and then sub-branches at a different angle. With repeated removal and reinsertion of the guidewire, the procedure is attended by the risk of significant trauma to the arterial lining, and in many cases, the obstruction cannot be reached at all with the guidewire and catheter.

Coronary arteries are tortuous and have many sub-branches. Often the obstruction is either located where the diameter of the artery is small or, by its very presence, the obstruction leaves only a very small opening through which a guidewire and/or catheter can be passed. Consequently the cardiologist often finds it very difficult to maneuver the guidewire or catheter, which is typically several feet long, from the proximal end.

In another application, Transluminal Laser Catheter Angioplasty (laser angioplasty), the delivery of laser energy from an external source to an intraluminal site to remove plaque or thrombus obstructions in vessels is accomplished by providing a waveguide such as a fiber optic bundle within a catheter. The nature of laser angioplasty requires even greater precision in control of the catheter, to position and aim the laser light at the specific plaques or thrombi to be removed.

These applications could all benefit from an increased degree of steerability of the tip of the guidewire or catheter from a remote site located external to the body. A variety of constructions have been proposed in the past to provide catheters which are steerable from the proximal end to enable the catheter to be aimed or advanced through non-linear cavities without removal for adjustments. Such constructions include those shown in U.S. Pat. No. 4,723,936 of Buchbinder; U.S. Pat. No. 4,921,482 of Hammerslag; U.S. Pat. No. 3,470,876 of Barchilon; U.S. Pat. No. 4,601,705 of McCoy, and others. These constructions involve shape memory alloy elements which may be heated to change their orientation, or devices employing wires or pulleys to steer the tip of a device from a handle located outside the body. However, each of these constructions has limitations.

Shape memory alloy devices have slow response due to reliance on heat transfer as the operative control mechanism. Also, shape memory devices in their superelastic state have a great deal of hysteresis, making them difficult to use for controlling position precisely. Devices making use of wires and or pullies for differential operation have problems achieving precise control over long distances, because long small diameter wires, requiring only minimal changes in length to actuate, do not afford very precise control. In addition, the cable tension required for such devices to work effectively dictates that the stiffness of the tip, which is critical to device effectiveness, is altered by the actuating mechanism. Also, the overall size of the device trades off against the ability to tension the cable, where the strain in the tensioned cable increases as device size decreases. It would therefore be desirable to achieve a remotely steerable catheterization device that does not incur penalties of stiffness, precision or size.

SUMMARY OF THE INVENTION

It is therefore an object of the invention to achieve a remotely steerable catheterization device that does not sacrifice desirable traits.

It is another object of the invention to achieve such a device that is scaleable to steer instruments of varying sizes.

It is another object of the invention to achieve a remotely steerable catheterization device that has a controllable stiffness over a portion of its length.

In accordance with one aspect of the present invention, there is provided an improved instrument, which may be either a steerable guidewire or a catheter implement of the type useful for percutaneous transluminal insertion into the coronary vascular system. Controlled negotiation of branches and turns to guide an angioplasty catheter or guidewire to an arterial stenosis or lesion or other treatment site is achieved without the need for prebending. The instrument achieves this performance by controlling deflection of the distal tip of the instrument in one or more planes through a wide and continuous range of angles. In accordance with another aspect, movement or positioning of an implement is enhanced by controllably stiffening a segment or portion of the implement.

In one embodiment of the present invention, a guidewire is provided having an elongate flexible shaft with a central lumen carrying one or more electrically insulated wires to a tip mounted on the distal end. The tip includes one or more layers of piezoelectric ceramic material bonded to opposite sides of a thin metal shim, the piezoelectric ceramic layers being poled and the electric signals from the wires attached such that a signal of one polarity causes one piezoelectric layer to extend, and the other piezoelectric layer to contract making the tip bend. The tip may include one or more pairs of oppositely straining piezoelectrics to produce tip flexing in one plane; a full three-dimensional range of motion is achieved by torquing the shaft, and moving it forward. Or, in a further embodiment, the tip may include an additional pair, or pairs, of oppositely straining piezoelectrics to produce tip bending in a second, orthogonal plane. A full 360 degree range of radial motion is then achieved by the combined action of the two pairs, all commanded remotely by signals extending from the proximal end of the device.

In another embodiment tip deflection is achieved by a lever-like tip with a piezoelectric element positioned eccentrically at the root of the tip to tilt or steer the lever.

In yet a third embodiment, a plurality of strain actuable elements are distributed along the length of the tip, and are selectively actuated to either induce a particular steering motion of the tip, to change the curvature of a portion of the tip, or to alter the stiffness of a portion in order to either advance, or anchor in place the position of the device.

The steerable device of the present invention thus negotiates tortuous and branched arterial systems, without the need for withdrawal and multiple insertions to deflect the tip.

BRIEF DESCRIPTION OF THE DRAWINGS

These and other features of the present invention will be understood from the following drawings of illustrative embodiments, taken together with the detailed description, wherein.

DETAILED DESCRIPTION

Figure 1:
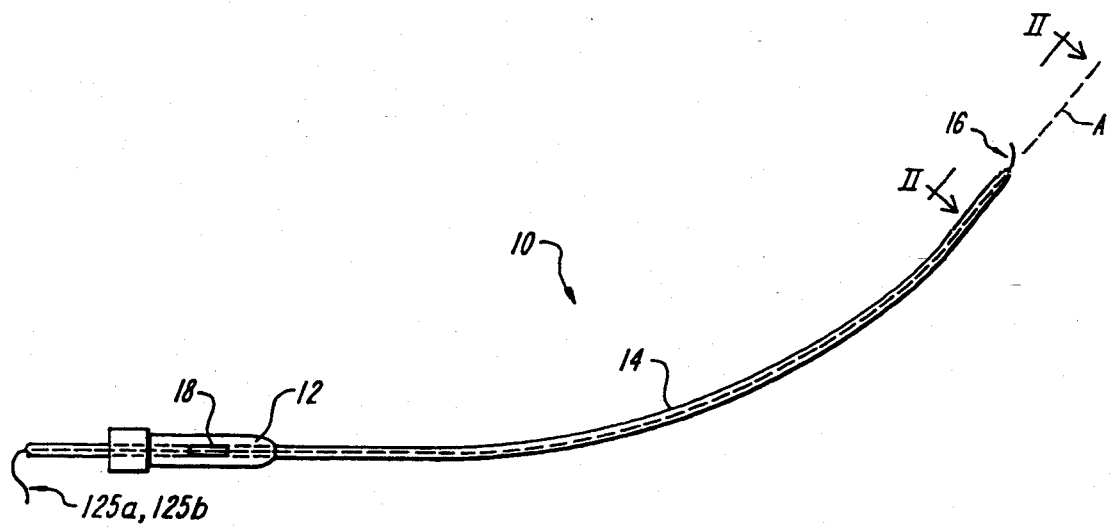
FIG. 1 shows a perspective view, partly in schema, of a steerable catheterization device according to the present invention.

FIG. 1 shows a steerable catheterization device 10 in accordance with the present invention, which includes a handle 12, an elongated body 14, and an active tip assembly 16 that is controlled by the handle. Device 10 may be, for example, a guidewire such as is commonly inserted preparatory to placing a catheter into a position near to a patient's heart, or may be a catheter itself, such as is commonly used, for example to insert a balloon to that region for angioplasty. The tip assembly is bent away from the nominal axis "A" of the body, by virtue of one or more active elements. While not specifically shown, the handle 12 includes a mechanism of conventional type, for example a spring loaded collet, that may be moved axially to grip the wire or body 14 and advance it inch by inch through the vascular system of a patient. The handle is preferably also adapted to rotate the wire as it advances, to steer the point of the off-axis tip assembly into branches or around curves as the body 14 is advanced along a vessel pathway. A control button 18 is ergometrically positioned on the handle 12 to control electrical actuation signals which are conducted through the body 14 to actuate the tip 16. This in turn controls the magnitude of off-axis deviation of the tip, or in some embodiments, the angle of tip direction in two planes or other tip characteristic.

Figure 3A:
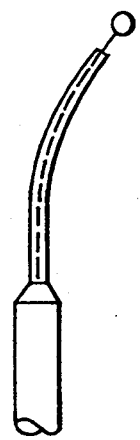
FIGS. 3A–3C show three different architectures of a guidewire or catheter tip.

As will be readily appreciated by those skilled in the art, the body 14 may be a guidewire, having a diameter of about 0.010 to 0.040 inches, a guide catheter having a diameter of about 0.060–0.135 inches, or other form of catheter or catheter-based device. The general form also mirrors that of certain other insertable instruments, e.g.; devices such as endoscopes and laparoscopy implements. Because of its small dimensions, a guidewire embodiment of the present invention offers the greatest challenges to implementation, and accordingly will be described below to best illustrate details of construction. The overall architecture of this tip is shown in FIG. 3A, and includes a piezoelectric bimorph mounted as a steerable wiggler at the end.

Figure 2:
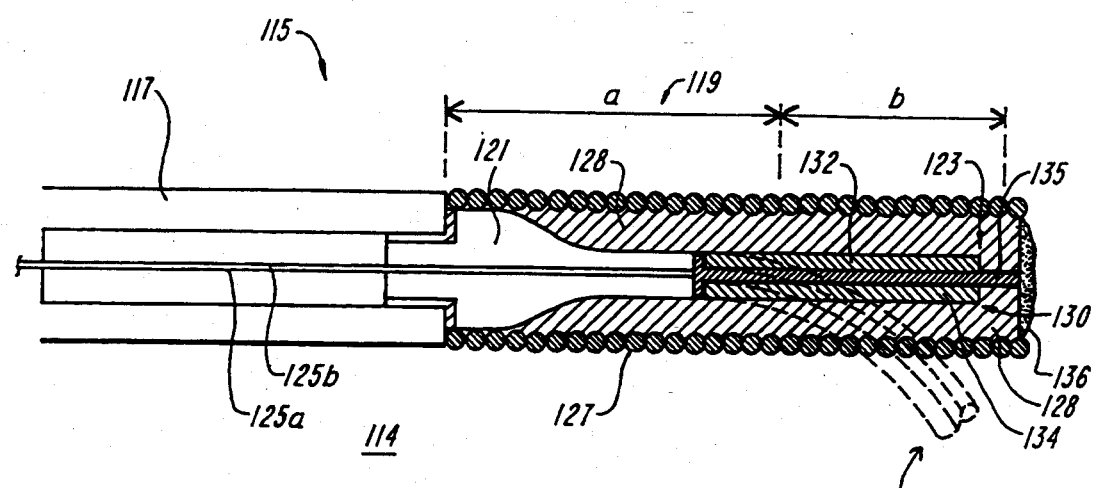
FIG. 2 shows a detailed axial cross section of the tip assembly of a device such as that of FIG. 1.

FIG. 2 shows a detailed cross-sectional view of the distal tip region 115 of one embodiment of a guidewire 114 in accordance with the present invention. Guidewire 114 includes a hollow wire body 117 approximately 36–48 inches long, and a steerable tip 119, which is approximately 5–10 inches long. By way of scale, body 117 is preferably formed of a thin metal tube, having an outer diameter illustratively 0.014 inches in diameter, with a wall thickness of 0.004–0.005 inches, leaving a four to six mil lumen. The tubular wall has a high degree of torsional and compressional stiffness to resist twisting and buckling, while allowing the body to bend freely as it is steered and pushed along the vascular system. A tapered nose piece 121 is attached to the end of the tube 117, and extends the internal lumen while tapering to a substantially smaller cross-section. Nose piece 121 may be formed of polycarbonate, stainless steel or the like. At the end of nose piece 121 an electrically actuated bending element 123 extends an additional one or two inches. Element 123 is actuated by one or more electrical conductors 125a, 125b which extend back through the body 117 to the control circuitry of the handle 12. The conductors are shown extending from the proximal end to the handle (FIG. 1), but in alternate embodiments, they may reside entirely within body 117, and connect to surface access pads which are distributed along the body at its proximal end. In this case, the handle contacts the pads to apply control signals to element 123.

Surrounding the nose piece and bending element is a biocompatible and flexible spiral winding 127 which may, for example, be formed of one to three rail diameter platinum wire. An electrically insulating potting agent 128, such as a silicone elastomer, fills the space 130 between the bending element 123 and the biocompatible winding 127. The three structures together—winding 127, potting medium 128 and the actuating element 123—have a high degree of flexibility comparable to that of a conventional (non-steered) guidewire. That is, the tip is floppy allowing the point to enter into branches and flex as it bumps its way around curves, while the elongated wire body 117 follows along. A thin outer shell or lubricous film such as polyurethane film (not shown), may encase the assembly to reduce friction of the device in the artery. By way of scale, the distances "a" and "b" may be, for example, two to seven inches, and one to two inches, respectively.

In accordance with a principal aspect of the invention, element 123 is electrically actuated by a driving voltage from outside to bend the tip off the longitudinal axis by an amount which, in the illustrated embodiment, is controlled up to a deviation calculated to exceed thirty degrees. A deflected position is indicated by "d" in phantom in the FIGURE. Greater deflections may be achieved by lengthening the element 123. Furthermore, the deflected tip may be rotated 360° about the longitudinal axis by torquing the insertion handle 12.

In the presently preferred embodiment of the invention, the adjustable element is fabricated out of piezoceramic plates, which are thinned to a dimension such that a completed multi-layer assembly made with the plates has a passive or non-actuated state bending stiffness comparable to the stiffness of a conventional wire steering tip, while remaining strong enough to deflect the tip when actuated.

In the illustrated construction, the electrically actuated element is formed with first and second strips of piezoelectric material 132, 134 bonded to opposite sides of a thin metal strip 135, and poled in opposite senses. The metal strip 135 serves as a common electrode for actuation of the elements, while wires 125a, 125b are connected to respective opposing plates.

To achieve a suitable flexibility, for a guidewire having a diameter under about fourteen mils, the plates 132, 134 may, for example, be formed of lead zirconium titanate, worked to a thickness of about one mil, and cut in strips six mils wide; the metal strip 135 may be about one mil thick, and also about six mils wide. The plates 132, 134 are 1-1½ inches long, and preferably the metal shim extends another half inch or more to the tip of the catheter or wire assembly. A solder dot 136 seals the end, enclosing the metal shim 135 and plates 132, 134 within the wire wrap, which as shown is filled with a potting medium 128. With this construction the fragile tip element is securely protected against fragments leaking out into the blood stream in the event of a fracture, while the entire tip assembly remains as supple and flexible as a prior art wire steering tip.

Electrical actuation of the device of FIG. 2 is performed via leads 125a, 125b which are connected to outer electrode surfaces of the plates 132, 134, and preferably also by the common electrode formed by the thin metal strip 135. The common electrode may be conductively connected to plated or metalized lines on the surface of the nose piece 121 (if a non-conductive material is used to form the nose piece) which, in turn, contact the conductive metal wire body 117, or may be connected to a separate insulated lead extending through the nosepiece.

As noted above, the dimensional limitations of a guidewire render the implementation of an active piezoelectric steering tip challenging. The thin plates of lead zirconium titanate are formed by taking commercial plates of small grain, low void lead zirconium titanate of greater thickness (e.g., 5, 7 or 10 mil plates as available from suppliers such as Edo, Morgan Matroc, or American Piezoceramics), bonding a plate with a high strength conductive adhesive to each side of a one rail metal sheet, to form a very high shear strength thin bonding layer, and then lapping the outer faces on an optical grinding or lapping jig to achieve a one mil thickness of each piezoceramic plate. The outer faces of each piezoceramic plate are then metallized, preferably with gold or other biocompatible metal to form electrode surfaces, and are then laser cut into strips six mils wide. After fabrication, the piezoceramic material is poled, by application of a high electric field between the conductive electrode faces. This produces a completed piezo bender unit for incorporation into the steering tip.

In addition to achieving a high degree of flexibility in the plates 132, 134, the thin dimensions result in an actuator that operates with low actuation voltages, so that full displacements are readily achieved with signals below thirty volts and one hundred fifty microamperes or less. This allows the device to be actuated by a current-limited electrical control signal, that is safe even in the event of leakage or a short circuit of wires 125a, 125b and body 117. In addition, sufficient actuation signals may be provided by batteries located within the handle 12.

In other embodiments, different piezoelectric elements may be used.

Figure 3B:
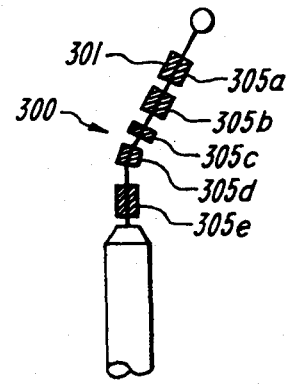
Figure 3C:
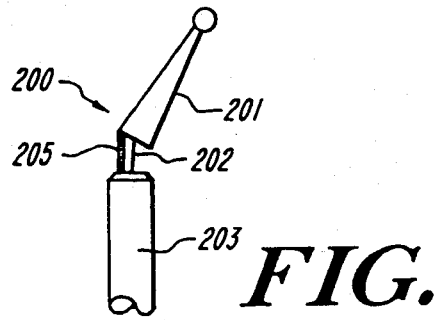

FIG. 3C illustrates an architecture wherein a steering tip 200 is formed by a lever arm 201 flexibly but inextensibly attached by a central wire 202 to a body 203 corresponding to the guidewire 117 of the preceding embodiment, or to a catheter. A piezoelectric post or stack 205 extends off-center and is operated in extension to rock the lever 201 to a desired angle. As in the preceding embodiments, the joint bearing the piezo element is preferably encased and encapsulated, e.g., by a sheath or wire wrap, and potting material.

FIG. 3B shows a third tip architecture 300. In this embodiment the bending tip 301 may be formed with a single metal shim extending the full length of the bending region (as in FIGS. 3A or 2), but a plurality of piezoceramic plates or sheet elements are positioned at discrete separated positions along the metal shim to induce different degrees of bending. As in the device of FIG. 2, the plates are arranged on opposite sides to form piezo benders which are localized along the tip length. When stiffness and dimensional constraints permit sufficient electrical leads, this embodiment may be actuated to undergo more complex bends, such as S-shaped bends, or may be actuated to bend at one position while stiffening the tip at a different position.

In accordance with a principal method of use of the present invention, the guidewire or catheter device is advanced within the vascular system of a patient, e.g., via the femoral artery, and is simultaneously visualized using a contrast medium under a fluoroscope. As the tip nears an arterial branch point or narrowed passage, control signals are applied from the handle to steer the tip, changing its direction as required to an appropriate angle or position, and the device is then rotated (if necessary for a one-dimensional deflector tip) and advanced further.

In accordance with another method of use in accordance with the invention, the tip may be actuated to assume an arc-shape that anchors it in position in a particular position, such as in in the aortic arch. For effecting this latter method, the active strain elements of the tip assembly are preferably mounted over an extended length, perhaps four to six inches, ahead of the tip area. In this case, the elements may be actuated to form a smooth arc of a radius that matches the arch curvature, so that the catheter resides in position without irritating the vessel walls. Alternatively, the elements may be actuated so that the catheter assumes a larger or smaller curvature, or has several polygonal bends, contacting the wall in several places to anchor it against sliding or creeping out of position.

Figure 7:
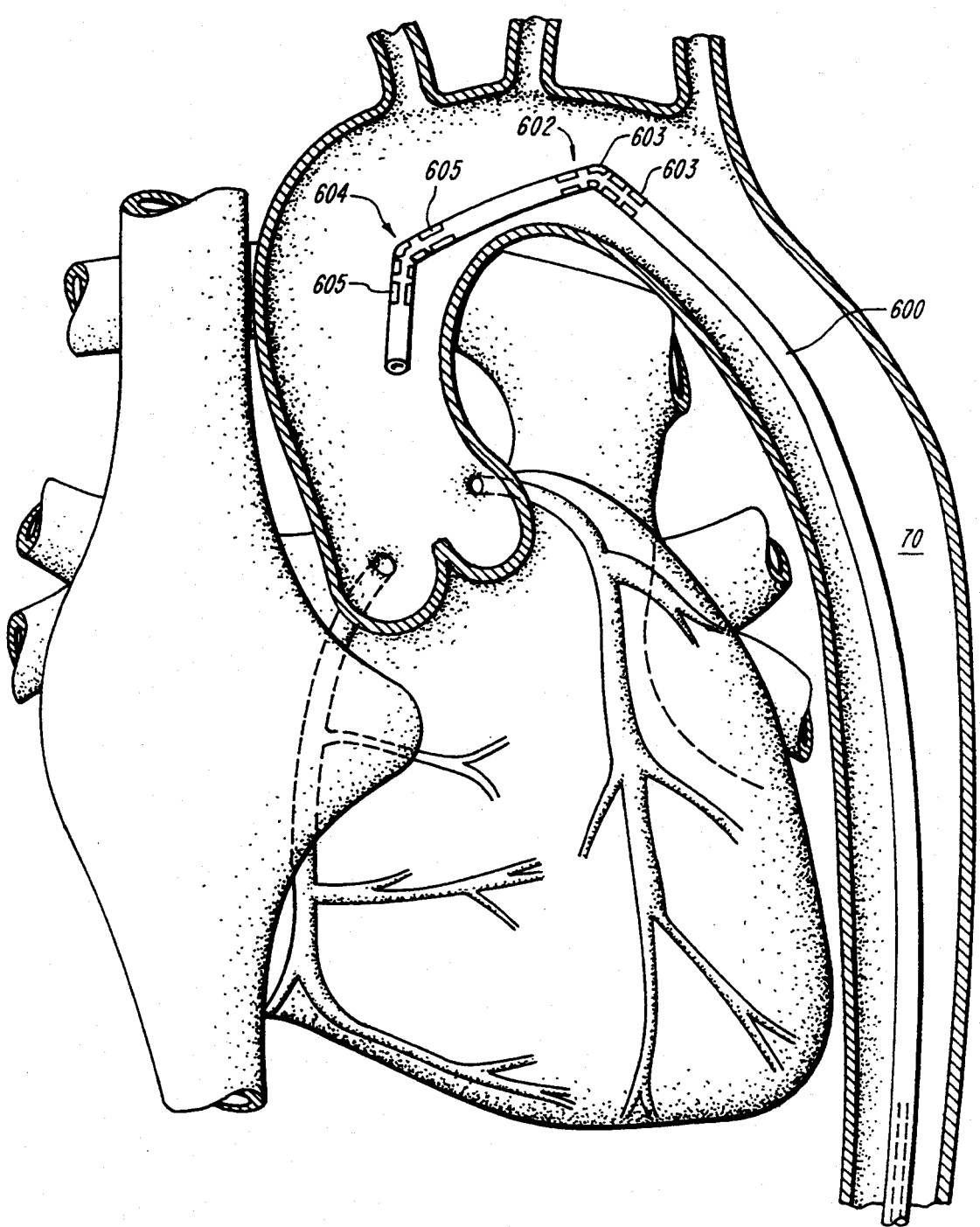
FIG. 7 shows a shaped guide catheter.

By way of particular example, the device may be a tube 600 as shown in FIG. 7 which is preformed to assume an arc-shape to position it in the aortic arch 70. Tube 600 has a pair of sharp bends or elbows, 602, 604 which are spaced to fit the arch, but which have relatively low bending stiffness, so that the tube readily straightens and passes through the patient's vessels during the insertion procedure. However, each elbow has respective piezoelectric strain elements 603,605 mounted about the elbow. These are actuated, once the tube has been positioned, to rigidify the bends and firmly lodge the tube in the desired position to support passage of coaxial catheters and wires within the lumen.

In accordance with yet a third method in accordance with the present invention, actuators may be energized to stiffen the tip or a portion of the tip assembly along its length to rigidify it for entering a branch point or passing an obstruction. Advantageously, by employing electrical signals to stiffen a region of the catheter or wire, the stiffness of the non-actuated positions of the wire or catheter body 117 remains flexible and unaffected.

Figure 4A:
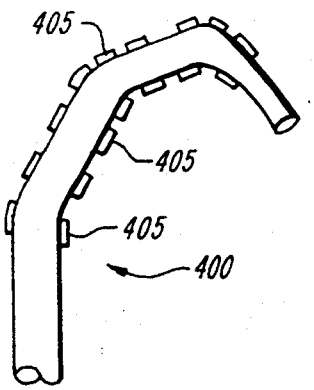
FIGS. 4A and 4B show two implementations of the tip architecture of FIG. 3B.
Figure 4B:
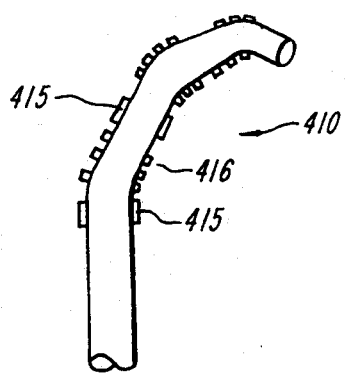

FIGS. 4A and 4B illustrate two methods of tip actuator placement, shown here for a guide catheter. In FIG. 4A a tip assembly 400 has a plurality of identically-sized strain actuators 405 placed on opposed sides of the tip at a number of equally-spaced intervals along its length, along a region where bending is desired, an inch or two from the end. In FIG. 4B, a tip assembly 410 has both larger strain elements 415 and smaller elements 416, which may be positioned to optimize one or more properties, such as to maximize deflection, avoid fracture of the elements, or speed up the response time of the actuator. Preferably, smaller elements are located at joint or flexure areas.

Figure 5A:
FIGS. 5A, 5B and 5C show three embodiments of the implementation of FIG. 4A.
Figure 5B:
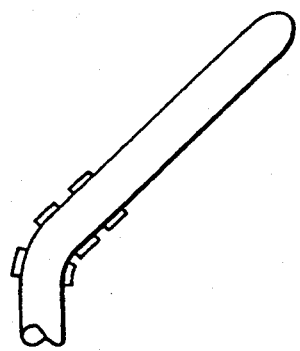
Figure 5C:
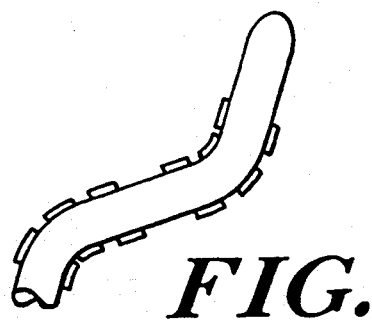

FIGS. 5A–5C illustrate variations in actuator placement along the tip, either at the extreme end (FIG. 5A), an inch or two back (FIG. 5B) or extending over a major segment of both regions of the end (FIG. 5C). In the latter case, elements at one position may be wired oppositely to those at another position to form a zig-zag rather than a single bend. Such shape, in conjunction with conventional torquing (rotation) of the wire or catheter body may offer enhanced vessel branch navigation abilities.

Figure 6:
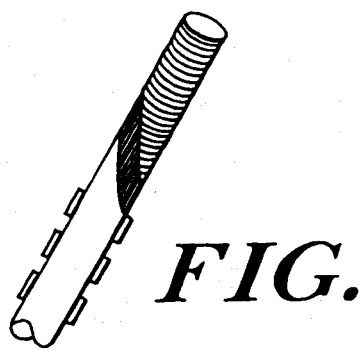
FIG. 6 shows details of an active tip fabricated with coil spring and lubricous coating.

Preferably the overall tip construction is a multi-layered construction as illustrated in FIG. 6, with an insulating but flexible sheath and a protective coil exterior, as described in respect of FIG. 2, above.

Figure 8A:
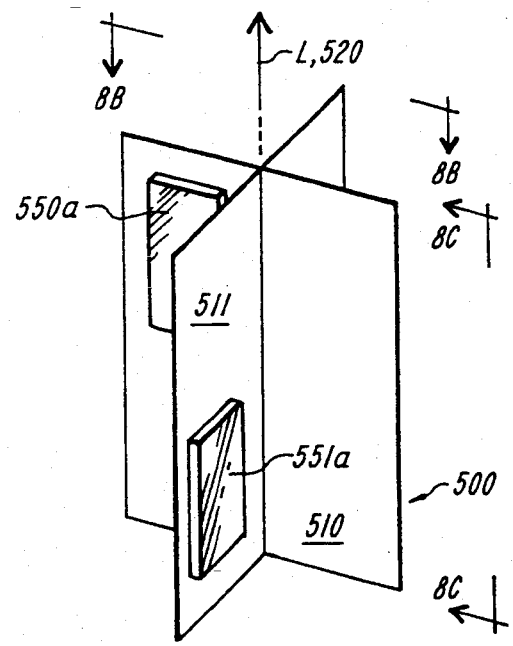
FIGS. 8A, 8B, and 8C show a steering tip bendable with two degrees of freedom about its longitudinal.
Figure 8C:
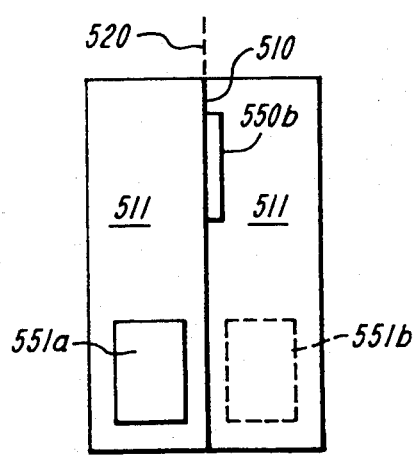
Figure 8B:
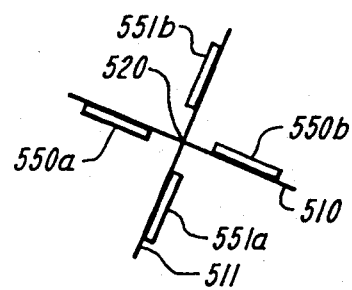

FIG. 8A, 8B and 8C illustrate, greatly enlarged, one embodiment of a tip construction 500 for bending along two degrees of freedom about the longitudinal axis "L" of a steered insertable device. First and second steel shims 510, 511 are mounted to cross each other as a pair of crossing vanes with oppositely-actuated strain elements 550a, 550b, and 551a, 551b positioned on the respective shims to deflect them in first and second planes, respectively. Geometric constraints due to the small geometry are largely avoided by mounting the strain actuators of each vane on opposite faces of the vane, and opposite sides of the vane's crossing axis 520. Furthermore, the actuators of the first vane are mounted at a different position along the axis L, than are the actuators of the second vane. Thus, as illustrated in perspective view FIG. 8A, the first set 550a, 550b bends the tip in the plane of the drawing, when actuated, while the second set causes out-of-plane deflections.

It will be understood that the constructions described above for guidewires, may be readily scaled to form an active steerable tip for a guide catheter, for a related instrument incorporating catheter or wire features, such as a balloon pump, or for an endoscope or specialized treatment device. In such cases, when devices are generally of greater diameter but the inner lumen must remain open, it may be desirable to use other strain actuated materials, such as polyvinylidene difluoride (PVDF), which may be bonded to the outside of the catheter, but below a protective layer. While generally capable of applying less force, PVDF actuators on larger tubes or catheters may benefit from the larger moment arm from the neutral axis. Further increases in mechanical advantage are obtained by mounting on the outer skin of the tube or catheter. Alternatively, one or more layers of a piezoelectric polymer material may form the tip body itself. In general, however, constructions using piezoceramics as described above, are preferred for their greater force characteristics and desirable low level signal requirements.

The invention being thus disclosed, further variations and modifications will occur to those skilled in the art, and all such variations and modifications are intended to be within the scope of the invention, as defined in the claims appended hereto.

What is claimed is:

1. A remotely steerable catheterization device, such device comprising
   an elongated body having proximal and distal ends, and being axially incompressible for advancing within a patient's body when pushed from the proximal end
   a steering tip at the distal end, said steering tip including a flexible shim and a piezoceramic strain element attached to the shim by high shear strength bonding, and
   electrical conductor means extending in said body from the proximal end to the steering tip for conducting electricity thereto
   wherein said strain element controllably deflects the steering tip in response to control signals applied thereto via said electrical conductor means to steer the tip past vessel branches from said proximal end.

2. A remotely steerable catheterization device according to claim 1, wherein said body is tubular.

3. A remotely steerable catheterization device according to claim 1, wherein said body is a guidewire.

4. A remotely steerable catheterization device according to claim 1, wherein said body is a guide catheter.

5. A remotely steerable catheterization device according to claim 1, wherein said body is a catheter having a lumen for effecting a diagnostic or treatment regimen at said tip via said lumen.

6. A remotely steerable catheterization device according to claim 1, wherein said strain element forms a piezoelectric bender.

7. A remotely steerable catheterization device according to claim 1, wherein said steering tip includes a lever arm that is displaced by actuating a piezoelectric element.

8. A remotely steerable catheterization device according to claim 1, wherein said strain element includes plural distinct strain actuators placed at axially-separated positions along said steering tip.

9. A remotely steerable catheterization device according to claim 8, wherein said plural distinct strain actuators include actuators of different sizes.

10. A remotely steerable catheterization device according to claim 8, wherein said strain element includes piezoelectric elements of a thickness to be fully actuated by a signal that is safe for cardiac applications.

11. A remotely steerable catheterization device according to claim 1, wherein said strain element has a stiffness approximating a stiffness of a cardiac catheterization guidewire.

12. A remotely steerable catheterization device according to claim 1, wherein said strain element forms a piezoelectric actuator extending over a substantial length of the tip for holding the tip in a stiff curve.

13. A remotely steerable catheterization device according to claim 1, further comprising a control handle operatively holding the elongated body for manipulation of the body by said control handle, and including first means for advancing the distal end by pushing said body.

14. A remotely steerable catheterization device according to claim 13, wherein said handle includes electrical means for applying electrical signals to said electrical conduction means.

15. An insertable catheterization device comprising
an elongated body having proximal and distal ends, for advancing within a patient's body when pushed from the proximal end
a steering tip at the distal end
electrical conduction means extending in said body for conducting electricity from the proximal end, and
a piezoceramic strain element means mounted by a shear-free coupling to a flexible shim in said device so as to receive electrical actuation signals via said electrical conduction means and bend the steering tip for physically controlling said device from its proximal end as it moves through branching vessels.

16. An insertable catheterization device according to claim 15, wherein said strain element means includes means distributed along the body for stiffening the body to lodge it securely in position within a vessel.

17. An insertable catheterization device according to claim 15, wherein said strain element means includes means distributed at said steering tip for actively bending the tip.

18. An insertable catheterization device according to claim 15, wherein said strain element means is a crystal.

19. A device for insertion into the body of a patient, such device comprising
an elongated flexible body including a tip
piezoceramic strain elements extending along at least a portion of the body and bonded by high shear strength coupling to produce a bending actuator of at least said portion of the body
conductive means for delivering a signal to the piezoceramic strain elements, and
control means for selectively providing said signal to the conductive means to physically control the portion covered by the strain elements.

20. An insertable catheterization device according to claim 15, further comprising an insulating flexible sheath enclosing said piezoceramic strain element means.

21. An insertable catheterization device according to claim 20, further comprising an exterior protective coil about said sheath.

22. An insertable catheterization device according to claim 19, wherein the strain elements are bonded to a metal shim in said portion.

23. An insertable catheterization device according to claim 22, wherein the metal shim is a common electrode of said strain elements.

24. A steerable catheterization device comprising
a long thin and flexible body including a flexible tip
said body including an inextensible element at said tip and a piezoceramic strain element which is actuated by applying a voltage across opposite sides thereof, said strain element extending adjacent the inextensible element to steer the tip when the strain element is actuated,
electrical conductors extending along said body for conducting electricity to the strain element, and
for selectively providing a voltage to said strain element to actuate the strain element and steer the tip in a desired direction.

25. A steerable catheterization device according to claim 24, wherein the strain element is a piezoceramic plate having a thickness to be fully actuated by a potential under thirty volts.

26. A steerable catheterization device according to claim 24, wherein the inextensible element is selected from a set including a shim or a pivot element.

* * * * *